US009688601B2

(12) United States Patent
Knebel et al.

(10) Patent No.: US 9,688,601 B2
(45) Date of Patent: *Jun. 27, 2017

(54) PROCESS FOR PREPARING (METH)ACRYLATES

(71) Applicant: Evonik Roehm GmbH, Darmstadt (DE)

(72) Inventors: Joachim Knebel, Alsbach-Haehnlein (DE); Ralf Merbach, Buettelborn (DE); Guido Protzmann, Bensheim (DE); Klaus Gottmann, Heppenheim (DE); John Hirsh, Fairhope, AL (US); Gerold Schmitt, Aschaffenburg (DE); Dieter Tessmer, Darmstadt (DE); Wilhelm Karnbrock, Bensheim (DE); Wolfgang Klesse, Mainz (DE); Volker Kerscher, Reinheim (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/924,018

(22) Filed: Oct. 27, 2015

(65) Prior Publication Data
US 2016/0046556 A1 Feb. 18, 2016

Related U.S. Application Data

(63) Continuation of application No. 12/745,703, filed as application No. PCT/EP2008/062982 on Sep. 29, 2008, now Pat. No. 9,206,270.

(60) Provisional application No. 61/014,927, filed on Dec. 19, 2007.

(51) Int. Cl.
*C07C 67/03* (2006.01)
*C08F 20/18* (2006.01)
*C08F 120/12* (2006.01)

(52) U.S. Cl.
CPC .............. *C07C 67/03* (2013.01); *C08F 20/18* (2013.01); *C08F 120/12* (2013.01)

(58) Field of Classification Search
CPC .............................. C08F 120/02; C07C 69/54
USPC ........................................................ 526/319
See application file for complete search history.

(56) References Cited

U.S. PATENT DOCUMENTS

| 6,639,099 | B1 * | 10/2003 | Knebel | .................. | C07C 67/03 560/217 |
| 9,206,270 | B2 * | 12/2015 | Knebel | .................. | C07C 67/03 |
| 2002/0143120 | A1 | 10/2002 | Yurugi et al. | | |
| 2003/0027881 | A1 | 2/2003 | Sunagawa et al. | | |
| 2004/0147772 | A1 * | 7/2004 | Schroder | .................. | C07C 67/03 560/4 |
| 2006/0144595 | A1 | 7/2006 | Milligan et al. | | |
| 2006/0148928 | A1 | 7/2006 | Harris et al. | | |
| 2007/0049768 | A1 | 3/2007 | Yurugi et al. | | |
| 2007/0240762 | A1 | 10/2007 | Harris et al. | | |
| 2008/0214858 | A1 | 9/2008 | Yurugi et al. | | |

FOREIGN PATENT DOCUMENTS

| EP | 0 882 739 | 12/1998 |
| EP | JP 11-49810 A | 2/1999 |
| EP | 1 201 641 | 5/2002 |
| GB | 2 163 149 A | 2/1986 |
| JP | 61-56155 A | 3/1986 |
| JP | 7-268054 A | 10/1995 |

(Continued)

OTHER PUBLICATIONS

Fujiwara et al., JP10175919 (A), Jun. 30, 1998; Human Translation.*
Office Action issued Oct. 26, 2015 in Japanese Patent Application No. 2014-190893 (with English language translation).
Office Action issued Jun. 3, 2013, in Japanese Patent Application No. 2010-538506 (submitting English translation only).

(Continued)

*Primary Examiner* — Sudhakar Katakam
*Assistant Examiner* — Kofi Adzamli
(74) *Attorney, Agent, or Firm* — Oblon, McClelland, Maier & Neustadt, L.L.P.

(57) ABSTRACT

Process for preparing (meth)acrylates of the formula (I)

$$CH_2=C(R^1)-CO-O-R^2 \qquad (I)$$

in which $R^1$ is hydrogen or methyl and
$R^2$ is a saturated or unsaturated, linear or branched, aliphatic or cyclic alkyl radical having 6 to 22 carbon atoms, or a $(C_6-C_{14})$-aryl-$(C_1-C_8)$-alkyl radical;
by reacting a (meth)acrylate of the formula II $$CH_2=C(R^1)-CO-OR^3 \qquad (II)$$

with an alcohol of the formula (III)

$$HO-R^2 \qquad (III)$$

in the presence of an amount of a suitable catalyst which catalyzes the reaction and of an amount of a phenolic polymerization inhibitor or a combination of two or more phenolic polymerization inhibitors which is sufficient to inhibit undesired polymerization;
the reaction being undertaken with input or introduction into the reaction mixture resulting from the reaction of an amount of oxygen or of an oxygenous gas mixture sufficient to inhibit undesired polymerization, and the process is characterized in that
the specific total oxygen input is less than or equal to 1.0 l/kg, measured in liters of oxygen per kilogram of (meth)acrylate of the formula (I), where the volume of oxygen introduced is calculated at a temperature of 25° C. and a pressure of 101 325 pascal.
The resulting (meth)acrylates can surprisingly be processed to particularly high molecular weight emulsion polymers which are, for example, outstandingly suitable for use as flow resistance reducers in mineral oil extraction.

20 Claims, No Drawings

(56) References Cited

FOREIGN PATENT DOCUMENTS

| | | | |
|---|---|---|---|
| JP | 9-31018 A | 2/1997 | |
| JP | 10175919 A * | 6/1998 | |
| JP | H10175919 A * | 6/1998 | ............ C07C 69/54 |
| JP | 11-80082 A | 3/1999 | |
| JP | 11-246479 A | 9/1999 | |
| JP | 2004-269417 | 9/2004 | |
| JP | 2006-104168 | 4/2006 | |
| JP | 2006-169220 | 6/2006 | |
| WO | 91 16037 | 10/1991 | |
| WO | 2005 040088 | 5/2005 | |
| WO | WO 2007/058310 A1 | 5/2007 | |

OTHER PUBLICATIONS

Japanese Observations by Third Party issued Mar. 18, 2013, in Japan Patent Application No. 2010-538506 (English translation only).
Translation of the Observations by Third Party in corresponding Japanese Patent Application No. 2010-538506 dated Dec. 27, 2013.
Kagaku Binran, Kiso-hen II. Katei 5-han, by Nippon Kagakukai (Handbook of Chemistry, Basic Ed. II, Revised $5^{th}$ Ed. By the Chemical Society of Japan), issue: Maruzen K.K., Feb. 20, 2004; II-54 [Publication A].
Fujiwara, JP 10175919(A), Jun. 30, 1998, Human Translation, 14 pages.

\* cited by examiner

PROCESS FOR PREPARING (METH)ACRYLATES

CROSS REFERENCE TO RELATED APPLICATION(S)

This application is a continuation of U.S. application Ser. No. 12/745,703, filed on Jun. 2, 2010, which is a 35 U.S.C. 371 national stage patent application of international patent application PCT/EP08/062982, filed Sep. 29, 2008, the text of which is incorporated by reference, and claims priority to U.S. Provisional Application No. 61/014,927, filed on Dec. 19, 2007, the entire content of which is incorporated herein by reference.

The present invention relates to a process for preparing (meth)acrylates, to (meth)acrylates prepared by this process and to their use for preparing high molecular weight homopolymers or copolymers.

Some processes for preparing (meth)acrylates are known (DE 3423441, DE 3430446, U.S. Pat. No. 5,072,027). (Meth)acrylates can be used, inter alia, as monomers to prepare polymer dispersions. What is especially desirable is the preparation of particularly high molecular weight polymer dispersions, since they can be used, for example, as flow resistance reducers in mineral oil extraction.

It is therefore an object of the present invention to provide an alternative process for preparing (meth)acrylate monomers which enables the monomers obtained to be particularly advantageously suitable for preparing high molecular weight polymer dispersions.

The present invention provides a process for preparing (meth)acrylates of the formula (I)

$$CH_2=C(R^1)-CO-O-R^2 \qquad (I)$$

in which $R^1$ is hydrogen or methyl and
$R^2$ is a saturated or unsaturated, linear or branched, aliphatic or cyclic alkyl radical having 6 to 22 carbon atoms, or a $(C_6-C_{14})$-aryl-$(C_1-C_8)$-alkyl radical;
by reacting
a (meth)acrylate of the formula II

$$CH_2=C(R^1)-CO-OR^3 \qquad (II)$$

in which $R^1$ and $R^3$ are each independently hydrogen or methyl;
with an alcohol of the formula (III)

$$HO-R^2 \qquad (III)$$

in which $R^2$ is a saturated or unsaturated, linear, branched or cyclic alkyl radical having 6 to 22 carbon atoms, or a $(C_6-C_{14})$-aryl-$(C_1-C_8)$-alkyl radical;
in the presence of an amount of a suitable catalyst which catalyses the reaction; and
in the presence of an amount of a phenolic polymerization inhibitor or a combination of two or more phenolic polymerization inhibitors which is sufficient to inhibit undesired polymerization;
the reaction being undertaken with input or introduction into the reaction mixture resulting from the reaction of an amount of oxygen or of an oxygenous gas mixture sufficient to inhibit undesired polymerization,
characterized in that
the specific total oxygen input is less than or equal to 1.0 l/kg, measured in liters of oxygen per kilogram of (meth)acrylate of the formula (I), where the volume of oxygen introduced is calculated at a temperature of 25° C. and a pressure of 101 325 pascal.

The $R^2$ radical in the alcohol of the formula (III) is understood, for example, to mean a hexyl, heptyl, octyl, 2-octyl, 2-ethylhexyl, nonyl, 2-methyloctyl, 2-tert-butylheptyl, 3-isopropylheptyl, decyl, undecyl, 5-methylundecyl, dodecyl, stearyl and/or behenyl radical, and/or a cycloalkyl radical such as cyclohexyl, tert-butylcyclohexyl, cycloheptyl, cyclo-octyl, bornyl and/or isobornyl.

$R^2$ is preferably a linear or branched alkyl radical having 8 to 12 carbon atoms, particular preference being given to the 2-ethylhexyl radical.

Moreover, the $R^2$ radical may be an optionally substituted $(C_6-C_{14})$-aryl-$(C_1-C_8)$-alkyl radical, preferably a $(C_6-C_{12})$-aryl-$(C_1-C_4)$-alkyl radical, for example the benzyl, naphthylmethyl, naphthylethyl, 2-phenylethyl, 2-phenoxyethyl, 4-phenylbutyl, 3-phenylbutyl, 2-phenylbutyl and/or the 2-biphenylethyl radical. Particular preference is given to the benzyl, 2-phenylethyl and/or 2-phenoxyethyl radical.

Alcohols of the formula (III) are known and are commercially available, for example, from Dow, Shell, Clariant or EOXO.

It is also possible to use mixtures of alcohols which stem from renewable raw materials or are obtainable from industrial synthesis processes, especially preferably mixtures of alcohols having n- and isoalkyl radicals having 6-22 carbon atoms.

The (meth)acrylate of the formula (II) is preferably methyl (meth)acrylate or methacrylic acid, preferably methyl methacrylate.

(Meth)acrylates of the formula (II) are obtainable commercially, for example from Röhm. Preference is given to the preparation of (meth)acrylates of the formula (I) in which $R^1$ is methyl.

The weight ratio of the alcohol of the formula (III) to the (meth)acrylate of the formula (II) is preferably in the range of 1:1.5 to 1:10, more preferably 1:2.5 to 1:5 and most preferably in the range of 1:3 to 1:4. Too small an excess can reduce the reaction rate; too great an excess is economically unviable since it reduces the utilizable tank volume.

To catalyse the present esterification or transesterification, it is possible to use catalysts, for example tetraisopropyl titanate, tetrakis(ethyl-hexyl) titanate, zirconium acetylacetonate, a dialkyltin compound, at least one lithium compound selected from the group of lithium oxide, lithium hydroxide, and lithium chloride, optionally in combination with a calcium compound selected from the group of calcium oxide and calcium hydroxide, or an acid (e.g. p-toluenesulphonic acid, sulphuric acid, methanesulphonic acid).

Preference is given to using tetraisopropyl titanate or tetrakis(ethylhexyl) titanate. These are commercially available, for example from Du Pont or Johnson Matthey Catalysts. The CAS number of zirconium acetylacetonate is 17501-44-9. The preparation of zirconium acetyl-acetonate from acetylacetone (pentane-2,4-dione) and zirconium compounds is described, for example, in Houben-Weyl, Methoden der organischen Chemie [Methods of organic chemistry], 4th edition, Vol. VI/2, 1963, pages 53-55 and 58 to 61, and in A. E. Martell, M. Calvin, "Die Chemie der Metallchelatverbindungen" [The chemistry of metal chelate compounds] (1958).

Advantageously, it is possible to use 0.2 to 10 mmol, more preferably 0.5 to 8 mmol, of catalyst per mole of alcohol of the formula (III).

The catalyst can also be prepared in situ, in which case the starting materials can be added to the reaction mixture before or during the esterification or transesterification.

The reaction can be effected at elevated or reduced pressure. In a particularly appropriate modification of the present invention, the esterification or transesterification can be performed at a pressure in the range of 200 to 2000 mbar, more preferably in the range of 500 to 1300 mbar.

The reaction temperature may, depending especially on the pressure, likewise be within a wide range. In a preferred embodiment of the present invention, the reaction is effected preferably at a temperature in the range of 80° C. to 140° C., more preferably 85 to 125° C.

Particular advantages can be achieved when the temperature at which the reaction is effected is increased in the course of the reaction.

The esterification or transesterification can be performed batchwise, semi-batchwise or continuously, preference being given to the continuous reaction.

It is also possible to initially charge a portion of the (meth)acrylate used for the transesterification not at the start of the reaction but rather only during the reaction.

The process according to the invention can be performed in bulk, i.e. without use of a further solvent. If desired, it is also possible to use an inert solvent.

These include petroleum, benzene, toluene, n-hexane, cyclohexane and methyl isobutyl ketone (MIBK), methyl ethyl ketone (MEK).

In the batchwise reaction regime of the process according to the invention, it is particularly appropriate to mix all components, for example the alcohol, the (meth)acrylate and the catalyst, and then to heat this reaction mixture to boiling.

In the case of transesterification, this first removes water which may be present in the alcohol in azeotropic form with the ester of the methacrylic acid. In the case of certain catalysts, it may be advantageous not to add the catalyst until after the water removal.

Subsequently, the alcohol released may be removed from the reaction mixture by distillation, if appropriate azeotropically. In the esterification, the water of reaction is removed, if appropriate as an azeotrope with a suitable azeotroping agent.

The pure reaction times are dependent upon factors including the parameters selected, for example pressure and temperature. They are, though, generally in the range of 1 to 10 hours, preferably of 1 to 5 hours and most preferably 1 to 3 hours. In the continuous process, the residence times are generally in the range of 0.5 to 5 hours, preferably of 1 to 4 hours, even more preferably 1 to 3 hours, especially 1 to 2 hours.

The reaction can preferably take place with stirring, in which case the stirring speed is more preferably in the range of 50 to 2000 rpm, most preferably in the range of 100 to 500 rpm.

In order to prevent undesired polymerization of the (meth)acrylates, a phenolic polymerization inhibitor or a combination of two or more phenolic polymerization inhibitors is used in the reaction. These compounds, for example hydroquinones, hydroquinone ethers such as hydroquinone monomethyl ether or di-tert-butyl-pyrocatechol, or sterically hindered phenols, are widely known in the technical field and are generally commercially available.

Particular preference is given to using hydroquinone and/or hydroquinone monomethyl ether.

The concentration of phenolic polymerization inhibitors in the (meth)acrylate of the formula I obtained by the process according to the invention should be kept as low as possible in order firstly to reliably prevent unwanted polymerization of the monomer and secondly to ensure the desired preparation of polymers with ultrahigh molar masses. This requirement is appropriately taken into account as early as in the preparation process.

The concentration of phenolic polymerization inhibitors is preferably <50 ppm, preferably <20 ppm, more preferably <15 ppm, especially <12 ppm (wt./wt.), based on the (meth)acrylate of the formula I.

The aforementioned concentration data are on the basis that the monomer has not been removed beforehand by distillation nor have further process steps been effected to remove the inhibitors (for example extraction, absorption on, for example, activated carbon or ion exchange resins).

When the monomer is removed by distillation or there follow process steps for removing the inhibitor, the concentration of phenolic polymerization inhibitors, according to the effectiveness of the process step, may be even higher, for example 10-1000 ppm. In this case too, the amount is preferably kept as low as possible in order to reliably prevent unwanted polymerization, i.e., for example, at 100-200 ppm (wt./wt.), lower if possible.

When the initiator is added, it is appropriate to charge not only the reaction vessel but also the column and, if appropriate, the condenser surfaces with inhibitors which can be metered, for example, into the column reflux line.

Oxygen is additionally used for inhibition. It can be used, for example, in the form of air, in which case the amounts are advantageously metered in such that the oxygen content in the gas phase is less than or equal to 18% oxygen (v/v), and is preferably below the explosion limit.

Particular preference is given to introducing an oxygenous gas mixture of oxygenous lean air having a content of less than or equal to 5% oxygen (v/v) into the reaction mixture.

Inert gas-oxygen mixtures, for example nitrogen-oxygen, argon-oxygen or carbon dioxide-oxygen mixtures, may likewise be used.

According to the invention, the specific total oxygen input is less than or equal to 1.0 l/kg, measured in liters of oxygen per kilogram of (meth)acrylate of the formula (I). The oxygen volume introduced per unit time is calculated from the volume flow and the oxygen content of the gas mixture introduced at a temperature of 25° C. and a pressure of 101 325 pascal. The volume flow of the gas mixture can be determined with suitable measuring instruments, for example with variable area measuring instruments (rotameters from Yokogawa). For the calculation of the specific total oxygen input, the period during which oxygen is introduced into the reaction mixture or the (meth)acrylate of the formula I at temperatures above 80° C. is employed.

The specific total oxygen input is preferably less than or equal to 0.5 liter of oxygen per kilogram of product of the formula (I), even more preferably less than or equal to 0.3 liter of oxygen per kilogram of product of the formula (I), especially less than or equal to 0.2 liter of oxygen per kilogram of product of the formula (I).

In the case of plants with a customary order of magnitude via production point of view (reactor volume ≥0.25 cbm-24 cbm), the oxygen is introduced by introducing air, preferably via a tube (diameter at the exit point, for example, 0.5-2 cm) which reaches down to close to the bottom in the interior of the reaction tank. The gas introduced by means of this apparatus flows through a liquid column of about 0.5-7 m which consists of the reaction mixture.

It has been found that, surprisingly, especially in the case of use of the above-described industrial or industrial scale reaction vessels, a significant difference in the specific viscosities and in the molecular weights of the emulsion polymers prepared from the monomers is observed when different amounts of oxygen are introduced into the reaction mixture during the preparation of the monomers. The specific viscosities and the molecular weights are increased to the desired degree when small amounts of oxygen are introduced (less than or equal to 1.0 l/kg, measured in liters of oxygen per kilogram of (meth)acrylate). When larger amounts of oxygen are added (greater than 1.0 l/kg, measured in liters of oxygen per kilogram of (meth)acrylate), undesirably low specific viscosities or molecular weights are obtained.

In a particular preferred embodiment, the process according to the invention is performed continuously and an oxygenous gas mixture of oxygenous lean air having a content of less than or equal to 5% oxygen (v/v) is introduced into the reaction mixture.

According to an appropriate embodiment of the present invention, in the case of the transesterification, the methanol released from the (meth)acrylate used can be removed by distillation. In this case, it is advantageously possible, for example, to remove a mixture which comprises methyl (meth)acrylate and methanol. A portion of the mixture removed can advantageously be recycled into the next batch. In this modification, the recyclable fraction of the mixture removed can be obtained towards the end of the reaction, especially after a conversion of 80%, preferably after a conversion of 90%. For example, the proportion of the mixture recycled to the start of the next batch may be in the range of 40 to 60%, based on the total weight of (meth) acrylate used.

In batchwise processes, excess reactant, especially the unconverted (meth)acrylate, can be removed by distillation towards the end of the reaction and be used again in the next batch without further purification.

The methanol-rich distillate obtained at the start of a transesterification can likewise be recycled, for example by incorporation into a plant, operated in an integrated system, for preparing the (meth)acrylate to be transesterified.

A suitable plant for performing the present esterification or transesterification may, for example, be a stirred tank reactor with a stirrer, steam heater, distillation column and condenser. Such plants are known per se and are described, for example, in Ullmann's Encyclopaedia of Industrial Chemistry (6th edition), publisher: Wiley-VCH, Weinheim 2003, volume 10, page 647. The size of the plant depends on the amount of methacrylate to be prepared, and the process according to the invention can be performed either on the laboratory scale (reactor volume 0.5-20 liters) or, particularly advantageously, on the industrial scale. In a particular aspect, the stirred tank reactor may accordingly have a tank volume in the range of 0.25 m$^3$ to 50 m$^3$, preferably 1 m$^3$ to 50 m$^3$, more preferably 3 m$^3$ to 50 m$^3$. In the case of the particularly preferred continuous preparation, the tank volume is preferably smaller and is, for example, 1-6 m$^3$. The stirrer of the reactor tank can be configured especially in the form of an anchor stirrer, impeller, paddle stirrer or inter-MIG stirrer.

The task of the distillation column is to ensure that a methanol-rich azeotrope is removed in order to minimize the losses of reactant ester which is inevitably also discharged. In the esterification, reactant and product components are retained for the benefit of the azeotroping agent-water azeotrope.

The distillation column may have one, two or more separating stages. The number of separating stages refers to the number of trays in a tray column or the number of theoretical plates in the case of a column with structured packing or a column with random packing. Examples of a multistage distillation column with trays include those such as bubble-cap trays, sieve trays, tunnel-cap trays, valve trays, slot trays, slotted sieve trays, bubble-cap sieve trays, jet trays, centrifugal trays; examples of a multistage distillation column with random packings are those such as Raschig rings, Lessing rings, Pall rings, Berl saddles, Intalox saddles; and examples of a multistage distillation column with structured packings are those such as the Mellapak type (Sulzer), the Rombopak type (Kühni), the Montz-Pak type (Montz). By virtue of the conversion-dependent adjustment of the reflux ratio, it is possible, for example, in the case of use of methyl methacrylate, to establish a methanol content in the distillate which is above 60% over wide ranges of conversion in the transesterification.

The suitable condensers which may be present in the plant for performing the present esterification or transesterification include plate and tube bundle heat exchangers.

After the reaction has ended, the resulting (meth)acrylate in many cases already satisfies the high requirements detailed above, such that further purification is in many cases not necessary. However, the product will preferably be isolated by distillation after the reaction has ended.

To further enhance the quality and especially to remove the catalyst, the resulting mixture can be purified by known processes. Owing to the polymerization tendency of the monomer, it is advisable to employ distillation processes in which the thermal stress on the substance to be distilled is minimized. Very suitable apparatus is that in which the monomer is evaporated continuously from a thin layer, such as falling-film evaporators and evaporators with a rotating wiper system. Short-path evaporators can also be used. Such apparatus is known (Ullmann's Encyclopaedia of Industrial Chemistry (6th edition), publisher: Wiley-VCH, Weinheim 2003, volume 36, page 505). For example, a distillation can be performed, in which a continuous evaporator with a rotating wiper system and attached column can be used. This distillation can be performed, for example, at a pressure in the range of 40 to 60 mbar and an evaporator temperature of 110° C. to 130° C.

The invention further provides a (meth)acrylate of the formula (I) obtained by the process claimed. It is characterized in that it contains preferably not more than 5 ppm, especially not more than 3 ppm, most preferably 1 ppm of polymerization inhibitors which do not require the presence of oxygen to inhibit the polymerization.

Polymerization inhibitors which do not require the presence of oxygen to inhibit the polymerization are understood, for example, to mean compounds of the formula IV

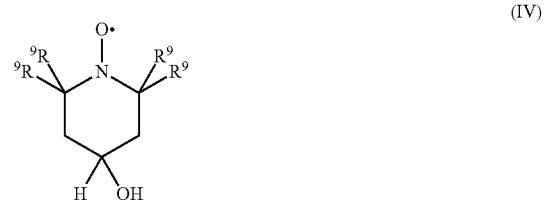

where the $R^9$ radicals are each independently a linear or branched alkyl radical, preferably having 1 to 6, especially having 1 to 4 carbon atoms, such as a methyl, ethyl, n-propyl, isopropyl, n-butyl, isobutyl or a tert-butyl radical, especially a methyl radical. A compound of the formula (IV) is sold under the name 4-hydroxy-2,2,6,6-tetramethylpiperidine 1-oxyl from Degussa GmbH and under the brand Tempol® by Ciba. Further compounds are, for example, 2,2-diphenyl-1-picrylhydrazyl, phenothiazine, N,N'-diphenyl-p-phenylenediamine, nigrosine (phenazine dye mixture), para-benzoquinone, or cupferron (ammonium salt of N-nitroso-N-phenylhydroxylamine or of phenylnitroso-hydroxylamine).

In addition, the (meth)acrylate of the formula (I) obtained by the process claimed preferably contains not more than 20 ppm, preferably not more than 15 ppm, most preferably 10 ppm of polymerization inhibitors.

The (meth)acrylates thus obtained can surprisingly be processed to give particularly high molecular weight homo- or copolymers which are outstandingly suitable for thickening liquids or for adjusting their flow properties, for example when used as flow resistance reducers in mineral oil extraction.

The invention therefore further provides for the use of at least one (meth)acrylate obtainable by the process according to the invention for preparing homo- or copolymers having specific viscosities $\eta_{spec/c}$ greater than or equal to 1000 ml/g, measured in THF. Particular preference is given to the preparation of homo- or copolymers having specific viscosities $\eta_{spec/c}$ greater than or equal to 1150 ml/g, especially $\eta_{spec/c}$ greater than or equal to 1300 ml/g, measured in THF. The monomer used is preferably 2-ethylhexyl methacrylate. Very particular preference is given to the preparation of 2-ethylhexyl methacrylate homopolymers. The specific viscosities $\eta_{spec/c}$ are determined on the basis of DIN 51562 in THF as a solvent. The concentration should be selected such that a relative viscosity in the range of 1.1-1.2 is achieved.

The monomers prepared by the process according to the invention may be copolymerized with one another in any ratios, provided that the resulting copolymer has the claimed specific viscosity in THF. In principle, it is also possible, though not preferred, to use a certain proportion of nonpolar non-acrylate monomers as comonomers to the generally nonpolar (meth)acrylate monomers, for example up to 50%, provided that they copolymerize sufficiently well with the (meth)acrylate monomers under the polymerization conditions used. Examples thereof are styrene, α-methylstyrene or long-chain vinyl esters such as vinyl versatate.

In this connection, "nonpolar" means the solubility of the monomers in demineralized water of <0.1 g/100 g at 20° C., without wishing to fix suitability strictly to this value.

The person skilled in the art can find information regarding copolymerization behaviour in standard works such as the Polymer Handbook ((4th edition), 1999, John Wiley & Sons).

What is crucial—and this is the case for polarity and copolymerization behaviour—is that the resulting copolymers have specific viscosities $\eta_{spec/c}$ of >1150 ml/g in THF. In this context, the use of more strongly polar (meth) acrylates as a comonomer is also not preferred, though not completely ruled out.

Suitable comonomers, which are not, however, limited thereto, are specified, for example, in WO 2006/073780 (pages 7-9), to which reference is made explicitly.

Polyunsaturated monomers are unsuitable as comonomers since they counteract expansion of the polymer aggregates by means of crosslinking.

Any customary polymerization process is suitable for preparing the homo- or copolymers, preference being given to emulsion polymerization. Processes for preparing high molecular weight (meth)acrylate polymers by emulsion polymerization are described, for example, in EP-A-555054, EP-A-882739 and WO 2006/081010.

The exact procedure in the emulsion polymerization of the inventive (meth)acrylate monomers of the formula I is uncritical, provided that conditions which lead to stable dispersions and to polymers with high molecular weights ($\eta_{spec/c}$ values) and good solubility in THF are maintained. The polymerization is preferably effected batchwise and is performed at low temperatures especially in the presence of a redox initiator system. A very low free-radical flow leads to the desired high $\eta_{spec/c}$ values. On the other hand, undesirably long inhibition periods can arise as a result in the case of inadequate oxygen exclusion and/or presence of inhibitors which are effective without oxygen.

The reaction mixture is selected such that the fully polymerized dispersion has a dry content of 20-65% by weight. The reaction mixture to be polymerized contains generally 35-80, preferably 50-60 parts by weight of water, and a total of 20-65, preferably 40-50 parts by weight of monomer and emulsifier, where the proportions by weight specified plus that of the initiator system and that of any buffer present add up to 100.00 parts by weight.

Preference is given to using purified water such as distilled or deionized water.

The reaction mixture may preferably also comprise at least one buffer. It is possible to use any buffer which is compatible with the initiator system used, for example carbonate, phosphate and/or borate buffer, in the generally customary amounts which are required to establish a particular pH.

The mixture is stabilized by means of emulsifiers and optionally by protective colloids.

The total amount of emulsifier is generally 0.1-10% by weight, 0.5-5% by weight, especially 0.5-3% by weight, based on the total weight of the monomer.

Particularly suitable emulsifiers are anionic or nonionic emulsifiers or mixtures thereof, especially:
  alkyl sulphates, preferably those having 8 to 18 carbon atoms in the alkyl radical, alkyl and alkylaryl ether sulphates having 8 to 18 carbon atoms in the alkyl radical and 1 to 50 ethylene oxide units;
  sulphonates, preferably alkylsulphonates having 8 to 18 carbon atoms in the alkyl radical, alkylarylsulphonates having 8 to 18 carbon atoms in the alkyl radical, esters and monoesters of sulphosuccinic acid with monohydric alcohols or alkylphenols having 4 to 15 carbon atoms in the alkyl radical; these alcohols or alkylphenols may optionally also be ethoxylated with 1 to 40 ethylene oxide units;
  phosphoric partial esters and their alkali metal and ammonium salts, preferably alkyl and alkylaryl phosphates having 8 to 20 carbon atoms in the alkyl or alkylaryl radical and 1 to 5 ethylene oxide units;
  alkyl polyglycol ethers, preferably having 8 to 20 carbon atoms in the alkyl radical and 8 to 40 ethylene oxide units;
  alkylaryl polyglycol ethers, preferably having 8 to 20 carbon atoms in the alkyl or alkylaryl radicals and 8 to 40 ethylene oxide units, especially $C_8$-$C_{12}$ alkylphenol ethoxylate;
  ethylene oxide/propylene oxide copolymers, preferably block copolymers, favourably having 8 to 40 ethylene oxide or propylene oxide units.

To stabilize the polymer dispersion, preference is given to using mixtures of anionic emulsifier and nonionic emulsifier, in which case the anionic emulsifier is advantageously initially charged and the nonionic emulsifier is added, if appropriate not until after the polymerization has ended. Mixtures of alkyl sulphates and $C_8$-$C_{12}$ alkylphenol ethoxylate in a weight ratio of 0.7 to 1.3 have been found to be very particularly useful.

Optionally, the emulsifiers may also be used in a mixture with protective colloids. Suitable protective colloids include partly hydrolysed polyvinyl acetates, polyvinylpyrrolidones, carboxymethylcellulose, methyl-cellulose, hydroxyethylcellulose, hydroxypropyl-cellulose, starches, proteins, poly (meth)acrylic acid, poly(meth)acrylamide, polyvinylsulphonic acids, melamine-formaldehyde sulphonates, naphthalene-formaldehyde sulphonates, styrene-maleic acid and vinyl ether-maleic acid copolymers. If protective colloids are used, they are preferably used in an amount of 3 to 5% by weight, based on the total amount of the monomer. The protective colloids may be initially charged before the start of the polymerization or be metered in. However, it should be ensured that the use of protective colloids does not impair the solubility in THF and the resulting specific viscosities. The use of protective colloids is therefore generally not preferred.

The initiation is effected with the initiators customary for emulsion polymerization. Suitable organic initiators are, for example, hydroperoxides such as tert-butyl hydroperoxide or cumene hydroperoxide. Suitable inorganic initiators are hydrogen peroxide and the alkali metal and ammonium salts of peroxodisulphuric acid, especially sodium peroxodisulphate, potassium peroxodisulphate or ammonium peroxodisulphate. The initiators mentioned may be used either alone or in combination with one or more reducing components.

Preferred redox partners of the initiators are transition metal salts having two oxidation states, for example iron sulphate and/or iron ammonium sulphate. When additional reducing components are used, for example bisulphites, metabisulphites, ascorbic acid, isoascorbic acid and sodium formaldehydesulphoxylate, catalytic traces of the transition metals are generally sufficient to trigger the polymerization, for example 10 ppm by weight based on the monomer. Without these components, generally higher concentrations of transition metals are required, for example 100 ppm by weight.

The initiator can be initially charged or metered in. In addition, it is also possible to initially charge a portion of the initiator and/or one component of the initiator system and to meter in the remainder or the other component. Preference is given to the latter.

The molar ratio of monomer to initiator is generally selected at a level as high as possible when the intention is to achieve high specific viscosities of the polymer. On the other hand, a required minimum amount of initiator arises from the requirements for a reliable and uniform polymerization and the length of the inhibition period. This minimum amount depends on the monomer quality, the content of polymerization inhibitors and on process conditions, such as the completeness of oxygen exclusion. It can be determined easily by a person skilled in the art by means of experiments.

The molar ratio of monomer to initiator is preferably $1\times10^3{:}1\text{-}5\times10^6{:}1$, especially $1\times10^4{:}1\text{-}2\times10^6{:}1$.

The molar ratio of the monomer to the reducing component is likewise preferably $1\times10^3{:}1\text{-}5\times10^6{:}1$, especially $1\times10^4{:}1\text{-}2\times10^6{:}1$.

The polymerization is preferably effected by the batch process. The polymerization temperature is generally 0 to 40° C., preferably 0 to 20° C., especially 0 to 10° C. The polymerization should take place with exclusion of oxygen, preferably in an inert gas atmosphere. For this purpose, an inert gas such as nitrogen is introduced continuously into the vessel containing the reaction mixture. Good mixing of the reaction mixture with the aid of a suitable stirrer should be ensured.

In the preferred embodiment, the initial charge in the reaction vessel comprises water, a buffer system, an anionic emulsifier, a first initiator component and the (meth)acrylate monomer, especially EHMA.

The polymerization is preferably started by adjusting the mixture to the polymerization temperature and metering in a second initiator component, preferably dissolved in water. The addition time of the dissolved initiator is generally 5 to 20 h. After the end of addition, it is possible to continue stabilization with a nonionic emulsifier.

In general, the monomer is polymerized up to a conversion of at least 95.0% by weight, especially at least 99% by weight, based in each case on the total weight of the monomer.

On completion of the polymerization, the (meth)acrylate homo- or copolymer can be removed from the aqueous dispersion by generally customary physical methods (for example filtering, centrifugation). In general, the removal of the polymers is preceded by a coagulation step, for example by electrolyte addition.

The high molecular weight (meth)acrylates thus prepared can be used in the form of aqueous dispersion directly as a thickener or as a drag reducer of crude oils and/or mineral oil fractions.

The examples which follow are intended to illustrate the invention without restricting it thereto.

EXAMPLES

Example 1

Preparation of 2-Ethylhexyl Methacrylate by a Batch Process

A 12 $m^3$ stirred tank reactor with stirrer, steam heater, distillation column and condenser is initially charged with 4200 kg of 2-ethylhexanol, 5000 kg of methyl methacrylate (MMA), 0.840 kg of hydroquinone monomethyl ether as an inhibitor and 28 kg of tetra-isopropyl titanate as a catalyst, which are stirred while constantly introducing air (14 $m^3$/h).

To stabilize the column, over the entire reaction phase, a total of 160 kg of MMA which contains 0.2 kg of hydroquinone monomethyl ether are metered into the column reflux. The mixture is heated to boiling temperature (beginning at approx. 90° C.), in the course of which the column is initially operated with full reflux. As soon as the temperature at the top of the column falls below 70° C., the methanol-MMA mixture formed is drawn off with variable reflux ratio (2:1-10:1). After approx. 3 hours and the removal of approx. 1200 l of methanol-MMA mixture, the reaction is very substantially complete (conversion >90%). As a result of the removal of the low-boiling components, the product temperature has risen to 116° C.

Up to a product temperature of 130° C., excess MMA is subsequently drawn off with a reflux ratio of 1:2 under standard pressure over a period of about 2 hours.

Thereafter, the MMA which still remains is removed completely under adjusted vacuum (1000-30 mbar) at a constant bottom temperature of 120° C. and without reflux. The air introduction is reduced to 4 $m^3$/h in the vacuum phase. When no further MMA distillate is obtained with the best vacuum over a period of 30 minutes, the vacuum is broken (duration about 2 hours).

The vessel contents, consisting of the catalyst-containing 2-ethylhexyl MA, are subsequently stabilized with 2.5 kg of Irganox 1076, and 2-ethylhexyl MA is distilled off with a reflux ratio of 1:10 under the best possible vacuum (approx. 30 mbar) and an average bottom temperature of 130° C.-140° C. The air introduction of 4 m³/h is maintained; the distillation step is complete after about 2 hours.

With a bottom residue of approx. 800 kg, 4900 kg of pure ester are obtained with the following composition (determined by gas chromatography):
2-ethylhexyl MA: 99.4%
2-ethylhexanol: 0.17%
MMA: 0.1%

Example 2

Preparation of 2-Ethylhexyl Methacrylate by a Batch Process

A 20 m³ stirred tank reactor with a stirrer, distillation column and condenser is initially charged with 8030 kg of methyl methacrylate (MMA), 7890 kg of 2-ethylhexanol, 364 g of hydroquinone monomethyl ether and 36 g of 4-hydroxy-2,2,6,6-tetramethylpiperidine 1-oxyl as inhibitors, and also 90 kg of 2-ethylhexyl titanate as a catalyst, and stirred with constant introduction of a gas mixture composed of 95% $N_2$ and 5% $O_2$ (10 m³/h).

To stabilize the column, over the entire reaction phase, a total of 908 kg of MMA which contain 908 g of hydroquinone monomethyl ether and 90 g of 4-hydroxy-2,2,6,6-tetamethylpiperidine 1-oxyl are metered into the column reflux. The mixture is heated to boiling temperature (approx. 100° C.). At a constant reflux ratio of 1:1, the methanol-MMA mixture formed is drawn off. During the reaction phase, 2800 kg of MMA are metered continuously into the reactor. After approx. 3 h, the reaction is very substantially complete.

Up to a product temperature of 130° C., excess MMA is subsequently drawn off at a reflux ratio of 0.2:1; the pressure is lowered continuously down to 40 mbar. The gas mixture introduction in the vacuum phase is reduced to 5 m³/h. The vacuum is broken when a pressure of 40 mbar is attained at a bottom temperature of 110° C. or higher (approx. 3 h). The tank contents are subsequently cooled to 80° C. and pumped into an intermediate tank.

The crude product is pumped out of the intermediate tank into a thin-film evaporator. The pure product is removed there at a pressure of 5 mbar. The product is condensed and collected in a tank.

A pure product is obtained with the following composition (determined by gas chromatography):
2-EHMA 99.1%
2-ethylhexanol 0.3%
MMA 0.5%

Example 3

Preparation of 2-Ethylhexyl Methacrylate by a Continuous Process

2-Ethylhexyl methacrylate is prepared continuously in a stirred tank battery consisting of three stirred tanks connected in series, each of capacity 2.1 m³, comprising a first column unit for removing the methanol-methyl methacrylate mixture formed and a second column unit for removing low-boiling components. The stirred tank battery is supplied continuously with 700 l/h of 2-ethylhexanol, 600 l/h of methyl methacrylate (MMA) and 15 kg/h of a 50% solution of 2-ethylhexyl titanate in MMA, which has been stabilized with 525 ppm of hydroquinone monomethyl ether.

Additionally metered into the system are 15 l/h of 3.5% hydroquinone monomethyl ether in MMA via reaction stage 1.

The individual reaction stages are supplied with stabilization air of in each case 450 l/h of fresh air. The vapours from the stirred tank which have been freed of methanol in the first distillation column are fed to the 1st stirred tank via the column bottom.

Under these reaction conditions (pressure 500 mbar), a reaction temperature of 107° C. is established in the first stirred tank. The reaction temperature is 125° C. in the 2nd stirred tank and 136° C. in the 3rd stirred tank.

The methanol formed is drawn off continuously as a methanol-MMA mixture at a rate of 240 l/h via the first distillation column with a circulation evaporator. The effluent of the 1st reaction vessel is passed on into the 2nd reaction vessel, and the effluent of the 2nd reaction vessel into the 3rd reaction vessel.

The effluent of the 3rd reaction vessel is fed continuously to the thin-film evaporator of the low boiler column, in which unconverted 2-ethylhexanol, MMA and methanol are drawn off as distillate (350 l/h) and fed back to the first distillation column.

The bottom effluent of the low boiler column is 1000 kg/h and has a composition of 98.1% 2-ethylhexyl methacrylate, 1.0% MMA and 0.7% 2-ethylhexanol and, to a smaller degree, high boilers and reactants.

Emulsion polymerization of 2-ethylhexyl methacrylate

The 2-ethylhexyl methacrylate prepared according to Examples 1 to 3 was in each case polymerized by emulsion polymerization.

To this end, 400 g of the 2-ethylhexyl methacrylate prepared were processed to an emulsion by means of an Ultra-Turrax at 4000 rpm for 3 minutes with

| | |
|---|---|
| 18 g | of sodium lauryl sulphate |
| 0.6 g | of $K_3PO_4 \cdot 3\ H_2O$ in 50 g of dist. water |
| 0.6 g | of $KH_2PO_4$ in 50 g of dist. water |
| 0.06 g | of ammonium peroxodisulphate (APS) in 50 g of dist. water |
| 373 g | of dist. water. |

The emulsion was transferred to the initial charge of a polymerization vessel which was cooled to circulation temperature 5° C. Simultaneously, nitrogen was introduced into the reaction mixture which was stirred at 100 rpm. Subsequently, the metered addition of a solution of 0.072 g $FeSO_4 \cdot 7\ H_2O$ in 100 g of dist. water over 20 hours was commenced. After the end of feeding, 24 g of Triton X 305 (70% strength) in 24 g of dist. water were added. Subsequently, the dispersion was filtered through a stainless steel screening fabric with MW 0.09 mm.

The specific viscosity $\eta_{spec/c}$ was determined based on DIN 51562 in THF as a solvent. The concentration was selected so as to achieve a relative viscosity in the range of 1.1-1.2. The particle radius was determined as the $r_{N5}$ value with an N5 Submicron Particle Size Analyzer from Beckman Coulter according to the manufacturer's instructions.

The analytical data of the monomers and of the polymer dispersions obtained from the monomers can be taken from the table which follows:

EHMA characterization and resulting homopolymer

| Monomer Example | Air/O2 content [%] on preparation | Total O2 input [l/kg EHMA] including degassing |
|---|---|---|
| 1 | 18 | 2.4 |
| 2 | 5 | 0.2 |
| 3 | 18 | 0.2 |

| | Stabilization of the monomer used | | TempolMA* | Characterization of the resulting polymer dispersion | rN5 | Dry content | |
|---|---|---|---|---|---|---|---|
| Example | HQME [ppm] | Tempol [ppm] | [PPM] | $\eta_{spec/c}$ in THF [ml/g] | [nm] | [%] | pH |
| 1 | 23.5 | — | — | 715 | 66 | 39.7 | 7.1 |
| 2 | 10 | <1 | 4.5 | 1464 | 52 | 39.6 | 7.2 |
| 3 | 1 | <1 | <1 | 1369 | 69 | 39.6 | 7.2 |

*TempolMA is a conversion product inevitably formed in the transesterification by reaction of Tempol with methyl methacrylate.

The invention claimed is:

1. A process for preparing a (meth)acrylate of formula (I)

$$CH_2=C(R^1)-CO-O-R^2 \quad (I)$$

wherein $R^1$ is hydrogen or methyl, and
$R^2$ is a saturated or unsaturated, linear or branched, aliphatic or cyclic alkyl radical having 6 to 22 carbon atoms, or a $(C_6-C_{14})$-aryl-$(C_1-C_8)$-alkyl radical,
the process comprising:
reacting a (meth)acrylate of formula II $$CH_2=C(R^1)-CO-OR^3 \quad (II)$$

wherein $R^1$ is hydrogen or methyl and $R^3$ is methyl,
with an alcohol of formula (III)

$$HO-R^2 \quad (III)$$

wherein $R^2$ is a saturated or unsaturated, linear, branched or cyclic alkyl radical having 6 to 22 carbon atoms, or a $(C_6-C_{14})$-aryl-$(C_1-C_8)$-alkyl radical,
in the presence of an amount of a suitable catalyst which catalyses the reaction and
in the presence of an amount of a phenolic polymerization inhibitor or a combination of two or more phenolic polymerization inhibitors which is sufficient to inhibit undesired polymerization, to form a reaction mixture,
the reaction undertaken with introduction into the reaction mixture resulting from the reacting, of an amount of oxygen or of an oxygenous gas mixture sufficient to inhibit undesired polymerization,
wherein
a specific total oxygen input is less than or equal to 1.0 l/kg, measured in liters of oxygen per kilogram of (meth)acrylate of formula (I), where the volume of oxygen introduced is calculated at a temperature of 25° C. and a pressure of 101,325 pascal,
and wherein the reacting is performed continuously.

2. The process according to claim 1, wherein the reacting of the alcohol of formula (III) to (meth)acrylate of formula (I) is carried out in a reaction vessel having a reactor volume of greater than or equal to 0.25 m³.

3. The process according to claim 1, wherein the (meth)acrylate of formula (I), after the reacting has ended, is isolated by distillation.

4. The process according to claim 1, wherein $R^2$ is a linear or branched alkyl radical having 8 to 12 carbon atoms or a $(C_6-C_{12})$-aryl-$(C_1-C_4)$-alkyl radical.

5. The process according to claim 1, wherein $R^2$ is a 2-ethylhexyl radical.

6. The process according to claim 1, wherein the catalyst is tetraisopropyl titanate, tetrakis(ethylhexyl) titanate, zirconium acetylacetonate, a dialkyltin compound, a lithium compound, optionally in combination with a calcium compound, or an acid.

7. The process according to claim 1, wherein the phenolic inhibitor is hydroquinone and/or hydroquinone monomethyl ether.

8. The process according to claim 1, wherein the oxygenous gas mixture introduced into the reaction mixture is oxygenous lean air having a content of less than or equal to 5% oxygen (v/v).

9. The process according to claim 1, wherein the specific total oxygen input is less than or equal to 0.5 liter of oxygen per kilogram of product of the formula (I).

10. The process according to claim 1, wherein the specific total oxygen input is less than or equal to 0.3 liter of oxygen per kilogram of product of the formula (I).

11. The process according to claim 1, wherein the specific total oxygen input is less than or equal to 0.2 liter of oxygen per kilogram of product of the formula (I).

12. The process according to claim 1, wherein the catalyst is tetraisopropyl titanate or tetrakis(ethylhexyl) titanate.

13. The process according to claim 1, wherein the catalyst is tetraisopropyl titanate.

14. The process according to claim 1, wherein the catalyst is tetrakis(ethylhexyl) titanate.

15. The process according to claim 1, wherein the catalyst is zirconium acetylacetonate.

16. The process according to claim 1, wherein the catalyst is a dialkyltin compound.

17. The process according to claim 1, wherein the process is performed without a further solvent.

18. The process according to claim 1, wherein a concentration of the phenolic polymerization inhibitor is less than 50 ppm, based on the (meth)acrylate of formula (I).

19. The process according to claim 1, wherein the alcohol of formula III and the (meth)acrylate of formula II are combined with the catalyst and polymerization inhibitor in a reaction vessel such that a weight ratio of alcohol of formula III:(meth)acrylate of formula II is in a range of from 1:1.5 to 1:10, to form the reaction mixture.

20. A process for preparing a (meth)acrylate of formula (I)

$$CH_2=C(R^1)-CO-O-R^2 \quad (I)$$

wherein $R^1$ is hydrogen or methyl, and $R^2$ is a saturated or unsaturated, linear or branched, aliphatic or cyclic alkyl radical having 6 to 22 carbon atoms, or a $(C_6\text{-}C_{14})$-aryl-$(C_1\text{-}C_8)$-alkyl radical, the process comprising:

reacting a (meth)acrylate of formula II $$CH_2\!=\!C(R^1)\!-\!CO\!-\!OR^3 \qquad (II)$$

wherein $R^1$ is hydrogen or methyl and $R^3$ is methyl, with an alcohol of formula (III)

$$HO\!-\!R^2 \qquad (III)$$

wherein $R^2$ is a saturated or unsaturated, linear, branched or cyclic alkyl radical having 6 to 22 carbon atoms, or a $(C_6\text{-}C_{14})$-aryl-$(C_1\text{-}C_8)$-alkyl radical, in the presence of an amount of a suitable catalyst which catalyses the reaction and in the presence of an amount of a phenolic polymerization inhibitor or a combination of two or more phenolic polymerization inhibitors which is sufficient to inhibit undesired polymerization, to form a reaction mixture, the reaction undertaken with introduction into the reaction mixture resulting from the reacting, of an amount of an oxygenous gas mixture sufficient to inhibit undesired polymerization, wherein a specific total oxygen input is less than or equal to 1.0 l/kg, measured in liters of oxygen per kilogram of (meth)acrylate of formula (I), where the volume of oxygen introduced is calculated at a temperature of 25° C. and a pressure of 101,325 pascal, the oxygenous gas mixture introduced into the reaction mixture is oxygenous lean air having a content of less than or equal to 5% oxygen (v/v), and wherein the reacting is performed continuously.

* * * * *